US010806411B2

United States Patent
Bauer (10) Patent No.: US 10,806,411 B2
(45) Date of Patent: Oct. 20, 2020

(54) X-RAY IMAGING SYSTEM AND METHOD FOR RECORDING X-RAY IMAGES

(71) Applicant: Siemens Healthcare GmbH, Erlangen (DE)

(72) Inventor: Sebastian Bauer, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 154 days.

(21) Appl. No.: 15/976,608

(22) Filed: May 10, 2018

(65) Prior Publication Data
US 2018/0325474 A1 Nov. 15, 2018

(30) Foreign Application Priority Data
May 10, 2017 (DE) .................. 10 2017 207 908

(51) Int. Cl.
*G01T 1/161* (2006.01)
*A61B 6/12* (2006.01)
(Continued)

(52) U.S. Cl.
CPC ............... *A61B 6/12* (2013.01); *A61B 6/04* (2013.01); *A61B 6/102* (2013.01); *A61B 6/44* (2013.01);
(Continued)

(58) Field of Classification Search
CPC ....... A61B 6/0407; A61B 6/00; A61B 5/0555; A61B 6/4441; A61B 6/4435; A61G 2210/50; A61N 2005/1057
See application file for complete search history.

(56) References Cited

U.S. PATENT DOCUMENTS

2008/0242944 A1 10/2008 Sharma
2009/0037049 A1* 2/2009 Clodfelter .............. A01B 63/00
701/36
(Continued)

FOREIGN PATENT DOCUMENTS

DE 102008016770 A1 10/2008
DE 102010032754 A1 2/2012
DE 102012212959 A1 1/2014

OTHER PUBLICATIONS

Nation et al. "The utility of handheld metal detector in detection and localization of pediatric metallic foreign body ingestion", Elsevier Ireland Ltd, 2016, p. 1-6 (Year: 2016).*
(Continued)

*Primary Examiner* — David P Porta
*Assistant Examiner* — Mamadou Faye
(74) *Attorney, Agent, or Firm* — Lempia Summerfield Katz LLC (57) ABSTRACT

For a particularly interference-free recording of x-ray images, an x-ray imaging system that includes an x-ray source for irradiating an examination object positioned in an examination region with x-ray radiation, and an x-ray detector for converting the x-ray radiation into image data of the examination object is provided. The x-ray source and the x-ray detector are arranged on an adjustable mount. The x-ray imaging system also includes a metal detection apparatus for detecting metal objects that are arranged at least partially within a field of view of the x-ray detector. A corresponding method includes receiving an instruction to record at least one x-ray image, activating the metal detection apparatus, and scanning the field of view of the x-ray detector for metallic objects using the metal detection apparatus. A display or a signal is output in the event of a detection of a metallic object.

17 Claims, 5 Drawing Sheets

(51) Int. Cl.
*A61B 6/00* (2006.01)
*A61B 6/04* (2006.01)
*A61B 6/10* (2006.01)

(52) U.S. Cl.
CPC .......... *A61B 6/4441* (2013.01); *A61B 6/5258* (2013.01); *A61B 6/5294* (2013.01); *A61B 6/542* (2013.01); *A61B 6/58* (2013.01)

(56) References Cited

U.S. PATENT DOCUMENTS

| | | |
|---|---|---|
| 2009/0299175 A1 | 12/2009 | Bernstein et al. |
| 2010/0189328 A1 | 7/2010 | Boernert et al. |
| 2011/0239770 A1* | 10/2011 | Yamano ............... G01N 29/043 73/632 |
| 2011/0257508 A1* | 10/2011 | Feuerlein ........... A61B 17/3403 600/411 |
| 2015/0085971 A1* | 3/2015 | Braun .................... A61B 6/032 378/8 |
| 2016/0324499 A1* | 11/2016 | Sen Sharma ......... G06T 11/008 |
| 2017/0209113 A1* | 7/2017 | Jackson ............... A61B 6/4266 |

OTHER PUBLICATIONS

German Office Action for German Application No. 102017207908.8 dated Oct. 30, 2017.

Mouton, Andre, et al. "An experimental survey of metal artefact reduction in computed tomography." Journal of X-ray Science and Technology 21.2 (2013): 193-226.

\* cited by examiner

X-RAY IMAGING SYSTEM AND METHOD FOR RECORDING X-RAY IMAGES

This application claims the benefit of DE 10 2017 207 908.8, filed on May 10, 2017, which is hereby incorporated by reference in its entirety.

BACKGROUND

The present embodiments relates to an x-ray imaging system with a metal detection apparatus and a method for recording x-ray images using an x-ray imaging system with a metal detection apparatus.

Modern stationary or mobile x-ray imaging systems with C-arms offer the possibility of intraoperative tomographic 3D imaging. To this end, the system uses the movable C-arm to acquire a set of two-dimensional projections from different viewing directions, from which a three-dimensional volumetric dataset is subsequently reconstructed using generally known methods. If metallic objects are located in the field of view of the two-dimensional projection recordings, which is determined by the C-arm projection geometry, then substantial image artifacts, referred to as metal artifacts in the following, arise due to various effects (e.g., enhanced beam hardening, enhanced scattered radiation, partial volume effect, increased noise) during the course of the reconstruction. The artifacts may adversely reduce the diagnostic quality of the reconstructed image.

Methods for minimizing metal artifacts may essentially be categorized into three groups: physical correction methods; sinogram interpolation methods; and iterative reconstruction methods (e.g., see the article by A. Mouton et al. *An experimental survey of metal artefact reduction in computed tomography*, Journal of X-Ray Science and Technology, Vol. 21, No. 2, pp. 193-226, 2013). In physical correction methods, an attempt is made to model the physical source of the error and to correct the error accordingly. Sinogram interpolation methods are based on the assumption that the x-ray beams, on the path of which a metallic object has been discovered, are generally unusable and are to be replaced by estimated values. Iterative reconstruction methods are often based on statistical approaches, in which the contribution weightings of beams, on the path of which a metallic object has been discovered, reduce and ultimately are also interpolated in an iterative method.

The methods for the correction of metal artifacts described above are based on the assumption that the metallic objects, which are located in the field of view of the two-dimensional projection recordings, are permanently and unavoidably connected to the examination object (e.g., a patient). In practice, this often involves metallic implants such as artificial joints, screws, wires, etc. In interventional imaging, for example, however, it has been found in practice that metal artifacts are often caused by metallic objects in the field of view of the two-dimensional projection recordings that are not permanently connected to the object to be examined. This may involve, for example, wires, catheters, cables, tools, or implants that for various reasons are located in the vicinity of the patient (e.g., mostly directly on the patient surface) and thus within the field of view of the projection recordings. The metallic objects may be moved away from the vicinity of the patient during or before the performance of an interoperative tomography scan and thus removed from the field of view of the projection recordings (e.g., at least temporarily for the duration of the recording). The presence of a metallic object is usually first recognized, however, based on the metal artifacts in the reconstruction volume, and thus only after the actual recording. Often, the recording is then to be repeated, whereby the accumulated patient dose doubles.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an x-ray imaging system that recognizes the presence of metallic objects even before the x-ray recording is provided. As another example, a method that enables a recording of x-ray images while avoiding interferences due to metallic objects is provided.

One embodiment of an x-ray imaging system includes an x-ray source for irradiating an examination object positioned in an examination region with x-ray radiation, and an x-ray detector for converting the x-ray radiation into image data of the examination object. The x-ray source and the x-ray detector are arranged on an adjustable mount (e.g., a C-arm). The x-ray imaging system also includes a metal detection apparatus for detecting metal objects that are arranged at least partially within the field of view (FOV) of the x-ray detector. By using a metal detection apparatus arranged on the x-ray imaging system in such a manner, a presence of a metallic object may be established even before the recording of an x-ray image. In this manner, the object may be removed if necessary and x-ray images that are free of interference may then be recorded. An examination object (e.g., a patient) is hereby protected from the risks caused by ionizing radiation (e.g., from unnecessary radiation exposure). The present embodiments may be in hybrid ORs, for example, in which a variety of metallic tools, wires, catheters, and cables conventionally find use; thus, the probability of a metallic object inadvertently being located in the field of view of the two-dimensional projection recordings (e.g., due to a lack of attention or knowledge on the part of the medical staff) increases. The field of view of the x-ray detector may be the entire region that may be captured by the x-ray detector (e.g., in an x-ray detector recording from a variety of projection directions, this is the entire three-dimensional region that may be captured by the x-ray detector). The field of view of the x-ray detector thus generally goes beyond the region to be reconstructed or the actual examination region. Metal objects that are located in the field of view of the x-ray detector outside the region to be reconstructed may also lead to interference in the reconstructed image.

According to one embodiment, the metal detection apparatus is arranged indirectly or directly on the mount (e.g., on the x-ray detector, on the x-ray source, or on a C-arm flange). In this manner, a detection particularly close to the object is possible, and an inspection for metallic objects may be performed, for example, from the perspective of the x-ray tube or the x-ray detector.

According to a further embodiment, the x-ray imaging system is formed by an angiography system that is embodied to record a variety of two-dimensional projection images and to reconstruct the projection images into a volume image.

A method according to one or more of the present embodiments for automatic metal inspection during the recording of x-ray images using an x-ray imaging system is provided. An instruction to record at least one x-ray image is received, and the metal detection apparatus is activated.

The field of view of the x-ray detector is canned for metallic objects by the metal detection apparatus, and a display or a signal is output in the event of a detection of a metallic object.

If x-ray images of an examination object are to be recorded and this is confirmed, for example, by a user, then the field of view of the x-ray detector is searched for metallic objects by the metal detection apparatus. If such a metallic object is discovered, then a related optical display or an acoustic or optical warning signal, for example, takes place in order to give the user the opportunity to remove the metallic object from the examination region.

The method according to one or more of the present embodiments increases the safety of radiation image recordings for a patient without interfering with the workflow in the process. The method prevents an unnecessary radiation exposure of the patient from having to take place if, for example, an x-ray recording is to be repeated because an interfering metallic object was present. Additionally, or as a result thereof, the image quality is improved.

According to a further embodiment, the acts of outputting a query regarding a continuation of the method, receiving a positive instruction or a negative instruction for continuing the method, and recording at least one x-ray image of the examination object in the event of a positive instruction are performed in addition. In this connection, the opportunity is also given to the user to select, taking into consideration the result of the metal detection, whether the user actually wishes to perform an x-ray image recording. The user may thus, for example, remove the metallic object after the completed signal and then issue an instruction to continue the method and perform the recording. Should the metallic object involve a non-removable object (e.g., implant), however, the user may also authorize a recording without removing the metallic object.

According to an alternative embodiment, the acts of repeating the activation of the metal detection apparatus and scanning the field of view of the x-ray detector (e.g., until a metallic object is no longer detected), and recording at least one x-ray image of the examination object in the event that no metallic object is detected (any more) are performed in addition. Different variants are possible, providing that an inspection may be undertaken after the simple scanning as to whether another metallic object has been found and, in the event of a negative, the recording may be actuated; in the event of a metallic object being found, either a signal is emitted or a further scanning takes place. In this manner, a recording is only performed if a metallic object is no longer present in the beam path.

Such a method is advantageous, for example, in the case of an x-ray imaging system, with which a variety of two-dimensional projection images are recorded and the projection images are then reconstructed into a volume image.

According to one embodiment, the act of activating the metal detection apparatus and scanning the field of view of the x-ray detector using the metal detection apparatus is performed during a test run for collision avoidance of the mount (e.g., the C-arm). In this manner, the metal detection may be skillfully adapted to a known workflow of an interventional imaging system, without taking up additional time. Test runs for collision avoidance of this kind are frequently to be performed as standard with movable C-arm systems (e.g., systems with articulated arm robots) prior to the actual recording in order to exclude possible collisions of the C-arm with the surroundings. In such test runs, no x-ray radiation is emitted, but rather, for example, the C-arm only moves along the trajectory provided for the actual recording.

For a particularly simple locating and thus rapid removal of the object, when detecting the metallic object, the position thereof is also ascertained.

According to a further development, the test run for collision avoidance runs through at least some (e.g., all) of the angulation positions of the mount for recording the projection images without the application of x-ray radiation. In this manner, a search for metallic objects may be undertaken even more precisely. Even a position determination of metallic objects may be performed in order to then remove the metallic objects in a rapid and targeted manner.

According to a further embodiment, the metal detection apparatus is formed by a metal detector probe. This captures whether metal is located within a defined measurement volume. A metal detector probe may be attached in different positions or orientations on or in the vicinity of the detector or on or in the vicinity of the x-ray source. This may involve a fluxgate magnetometer, for example.

According to a further embodiment, the metal detection apparatus is formed by at least one (e.g., two) metal detector measuring cabinets.

These capture whether metal is located within a defined measurement volume (e.g., between the two measuring cabinets). The two components of the measuring cabinets may, for example, be attached in different positions or orientations in the vicinity of the detector and in the vicinity of the x-ray source.

In an x-ray imaging system with a patient couch for positioning the examination object, the metal detection apparatus may be arranged on or in the patient couch.

The x-ray imaging system may be formed by an angiography system that is embodied to record a variety of two-dimensional projection images and to reconstruct the projection images into a volume image.

DETAILED DESCRIPTION

Figure 1:
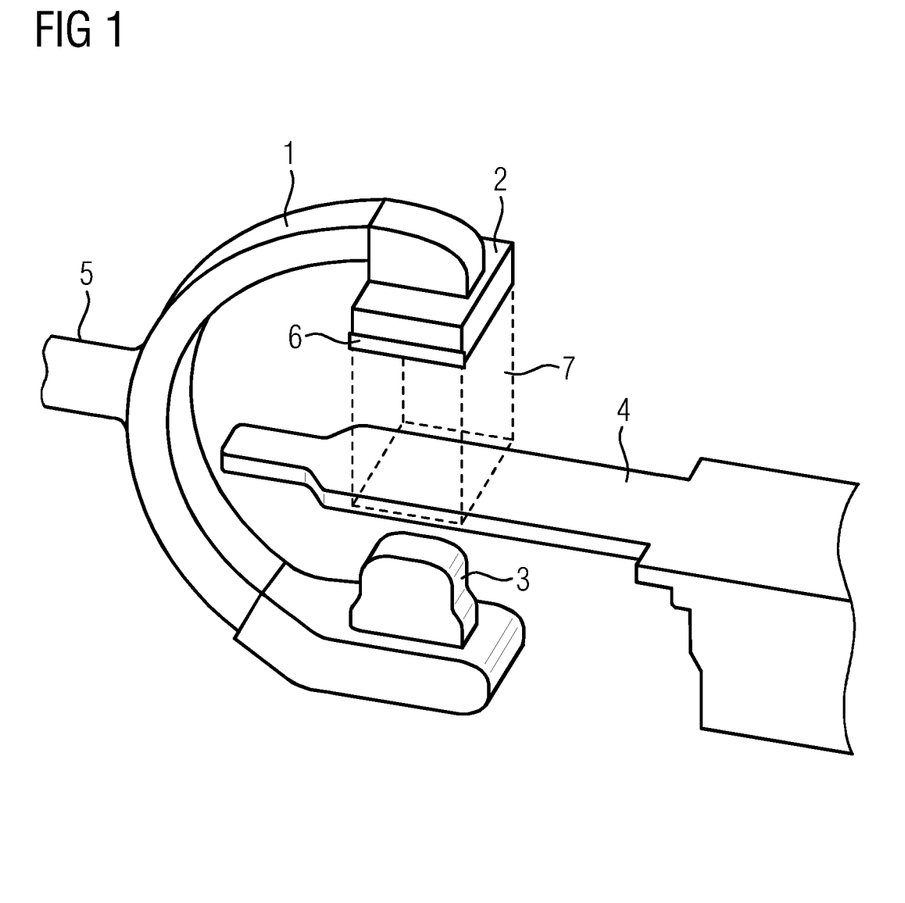
FIG. 1 shows a view of one embodiment of an x-ray imaging system with a metal detector probe.

A cutout of an x-ray imaging system with a C-arm 1 is shown in FIG. 1. The C-arm 1 is able to move in space (e.g., three-dimensionally; by being fastened to an articulated arm robot). An x-ray source 3 and an x-ray detector 2 are arranged on the C-arm 1. The C-arm 1 is connected to a remaining part of the x-ray imaging system via a C-arm flange 5. The x-ray imaging system has further components, such as a patient couch 4, a system controller, an image processing computer, input apparatuses and monitors, etc. Many of these components are not shown here. Arranged on the x-ray detector 2 is a metal detection apparatus (e.g., a metal detector) in the form of a metal probe 6. Metal probes of this kind may, for example, be embodied in the form of fluxgate magnetometers, Hall sensors, or xMR sensors (x-magnetoresistive) or another possible form. Metal probes are commercially available in many forms. The metal probe 6 is in a position to detect metal in a certain spatial region (e.g., a measurement volume 7). The measurement volume 7 includes an entire three-dimensional field of view of the x-ray detector that may be captured by the x-ray detector at any possible angulation, possibly an even greater spatial region. The metal probe 6 is attached to one of the sides of the x-ray detector (e.g., at a right angle to a sensor surface of the x-ray detector 2). Any other desired positions or orientations on the x-ray detector 2 may also be provided, however, as long as an impairment of the x-ray detector 2 is excluded and a coverage of the measurement volume 7 with regard to a metal detection is provided.

Figure 2:
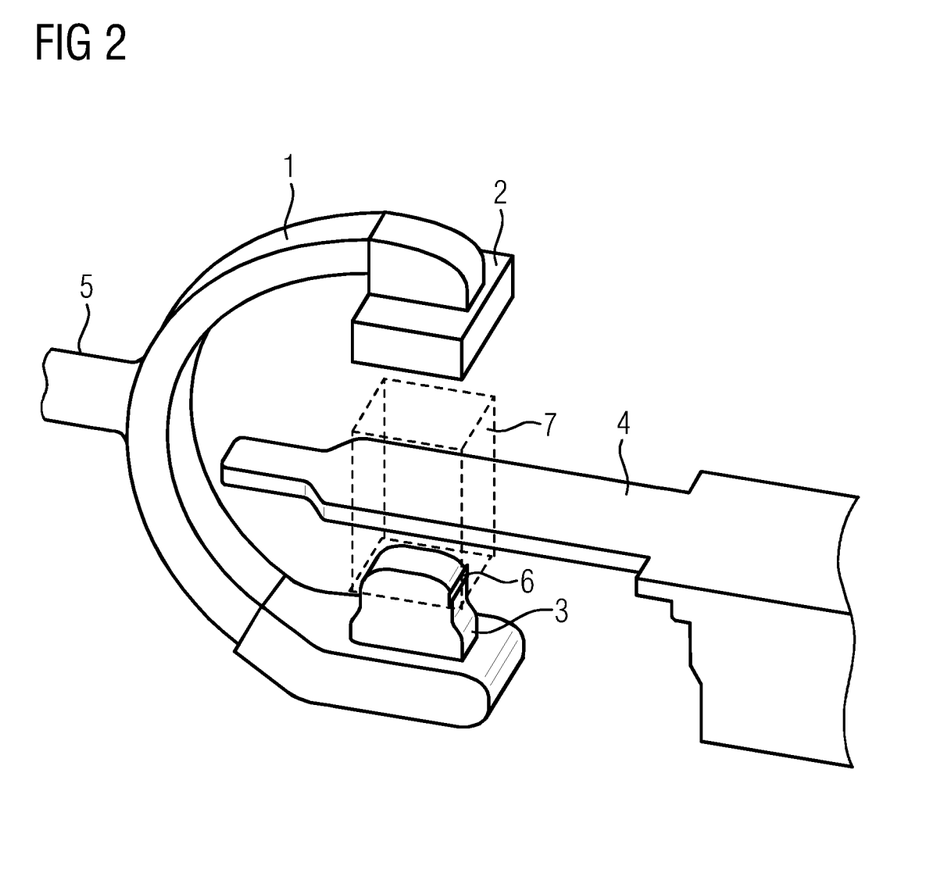
FIG. 2 shows a view of one embodiment of an x-ray imaging system with a metal detector probe.

A cutout of an x-ray imaging system with a C-arm 1, in which the metal probe 6 is arranged on the x-ray source 3, is shown in FIG. 2. A lateral arrangement may be provided, but any other positioning that excludes an impairment of the x-ray source 3 may be provided. Further possibilities not shown are, for example, in the vicinity of the C-arm flange 5 or at another position of the C-arm 1. Highly sensitive metal probes for detection of very small objects are known and available from the prior art. In one embodiment, metal probes that do not penetrate into the patient may also be used. The detection of metallic objects in the body may also be dispensed with, for example, if the objects cannot be removed.

Figure 3:
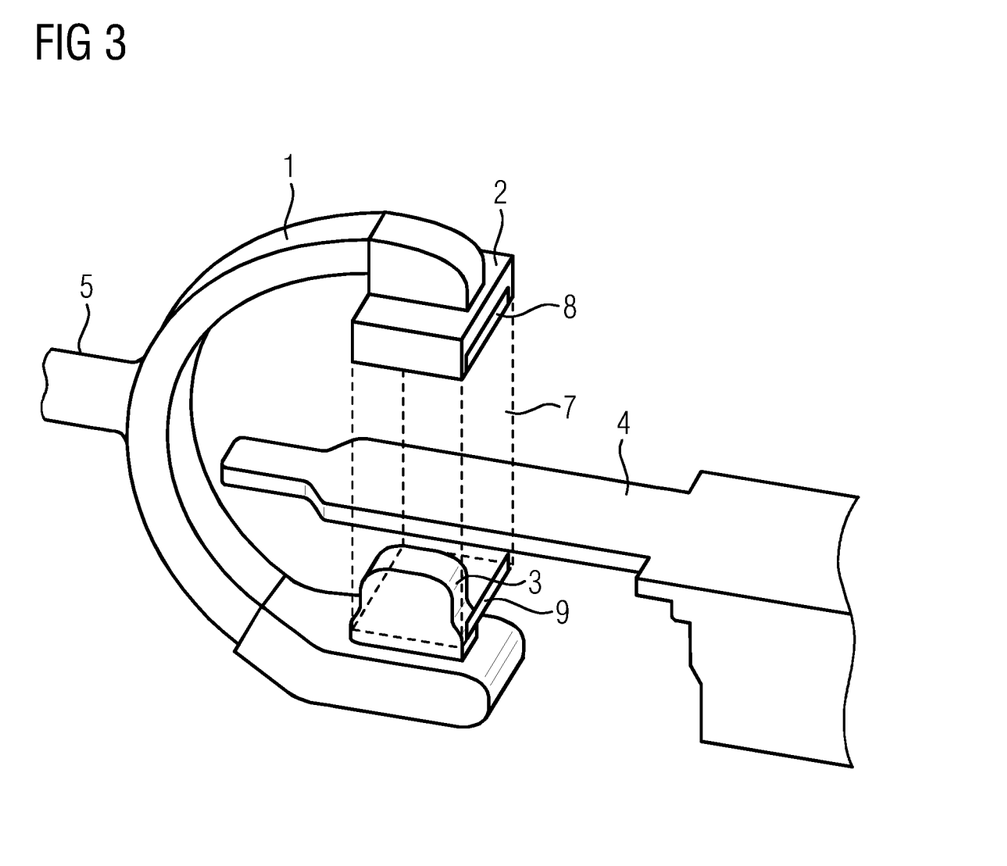
FIG. 3 shows a view of one embodiment of an x-ray imaging system with a metal detector cabinet.
Figure 4:
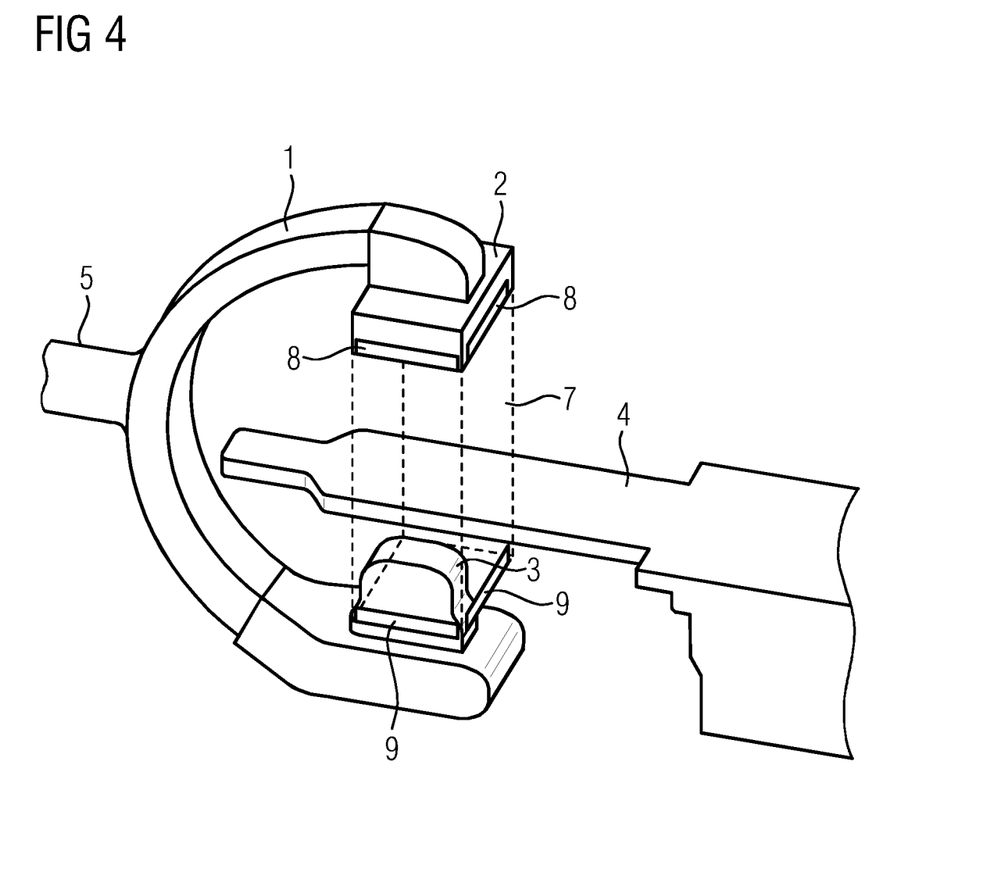
FIG. 4 shows a view of one embodiment of an x-ray imaging system with two metal detector cabinets.

In FIGS. 3 and 4, at least one measuring cabinet that is constructed from a first part 8 and a second part 9 (FIG. 3) or two measuring cabinets (8, 9; FIG. 4) are arranged on an x-ray imaging system as metal detection apparatuses. These capture, in a known manner, whether metal is located within a defined measurement volume 7 between the first part 8 and the second part 9 of the measuring cabinet. The first part 8 and the second part 9 of the measuring cabinets may, for example, be arranged in different positions or orientations on or in the vicinity of the detector or on or in the vicinity of the x-ray source. Measuring cabinets as such and the measurement principle thereof for the detection of metal are known and are used in many fields (e.g., in airports for security control). More than two measuring cabinets may also be present.

A further alternative embodiment makes provision for the integration of a metal probe or measuring cabinet or a component of the measuring cabinet in the patient couch 4.

In one or more of the present embodiments, the measurement volume 7 of the metal detection apparatus is set so that the measurement volume 7 covers at least the three-dimensional field of view of the x-ray detector. This provides that metallic objects that are located in the field of view of the two-dimensional projection recordings are detected. In addition to a general detection of whether a metallic object is located in the three-dimensional field of view of the x-ray detector, a precise position and orientation detection of the metallic object may also take place. In this manner, the user may remove the metallic object even more simply.

Figure 5:
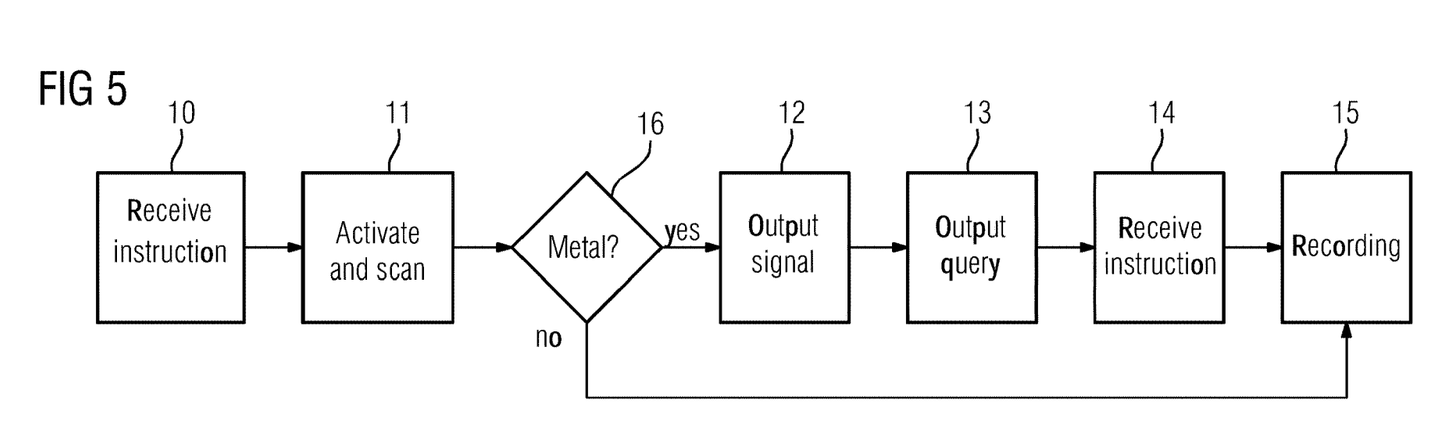
FIG. 5 shows a flowchart of one embodiment of a method.

In FIG. 5, a flowchart for a method according to one or more of the present embodiments for automatic recording of x-ray images using an x-ray imaging system is shown. In act 10, an instruction to record at least one x-ray image is received. For this purpose, for example, an input apparatus, a keyboard, a touch screen, or a microphone may be provided, and the instruction is input by a user of the imaging system through the input apparatus and thereby transferred to the imaging system. The instruction is then, for example, transferred to the system controller thereof. In act 11, triggered by the input, the metal detection apparatus is activated, and at least the three-dimensional field of view of the x-ray detector is scanned for metallic objects. If a metallic object is detected, in act 12, a display or a signal is then output by the imaging system. For this, a simple optical signal may be output (e.g., on a display unit such as a monitor), but an accurate representation of the field of view of the x-ray detector and the position of the metallic object may also be shown. Alternatively, an acoustic signal or a colored/flashing light also may be indicated in a simple manner. The user receives the corresponding information that a metallic object is present and gains the opportunity to remove the metallic object from the field of view as far as possible.

Following this, in act 13, controlled by the system controller, for example, a related query is output as to whether the user desires to continue the method or perform the x-ray recording. In act 14, a corresponding input by the user is received. The corresponding input includes a positive instruction or a negative instruction regarding a continuation of the method. If the instruction is a confirmation that a continuation is desired, then in act 15, the recording of the x-ray image(s) is initiated and one or more corresponding recordings are produced. By way of the query, the user receives the opportunity to continue the x-ray recording in spite of the detection of a metallic object. The user may have, for example, previously removed the metallic object for the short or long term or, however, may have established that a non-removable object (e.g., implant) is involved and the recording therefore should be produced in spite of the metal in the beam path. In one embodiment, there may also be provision for the user, by way of user input, to cancel the method, prevent the x-ray recording, or initiate a repetition of the method from the beginning (e.g., scanning the field of view of the x-ray detector) for further inspection. If no metallic object is detected during the act 11, then the performance of the x-ray recording may be continued with directly.

Figure 6:
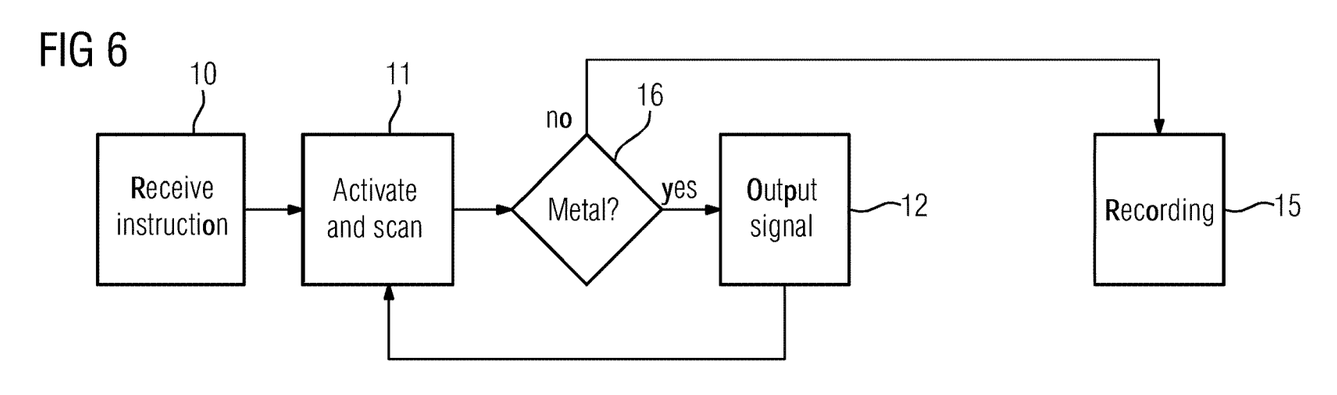
FIG. 6 shows a flowchart of another embodiment of a method.

Alternatively, the method may be continued as follows with the presence of a metallic object after the act 12: After the output of a signal or the display, the act 11 is repeated (e.g., the metal detection apparatus is activated once again, and the examination region is scanned). If a metallic object is no longer found, then it is possible to skip directly to act 15, the performance of the x-ray recording. If a metallic object is detected again, then act 12 (e.g., the signal output or display) may be repeated, and the act 11, the activation of the metal detection apparatus and the scanning of the field of view of the x-ray detector, may then be repeated. This loop may be run through for as long as until a metallic object is no longer detected. Alternatively, a user may then also cancel the method.

The measurement of the metal detection apparatus may take place either based on the current mechanical configuration of the adjustable mount or C-arm (e.g., position, angulation, etc.) or based on a predefined configuration. The measurement may also be integrated into the existing course of an interventional 3D imaging in a time-saving manner. Thus, the measurement may be executed, for example, over the course of a test run of the mount/the C-arm, which may take place before the actual 3D x-ray recording without x-ray radiation in order to exclude possible collisions of the mount/the C-arm. During the test run, the object is generally observed from different sides, which provides that the metal detection rate may be improved if necessary.

Metal detection apparatuses that not only supply the information of whether metal is present, but rather even localize the metallic objects in a spatial measuring grid and indicate the material quantity and the material type are known. If the in effect two-dimensional position of the metallic object is captured during the test run from different angulations (e.g., projection directions relative to the examination object), then the three-dimensional position may be extrapolated in a more precise manner.

Although the method requires additional acts within the clinical workflow, the makes it possible to avoid dose-intensive recording beforehand, which due to metal artifacts, ultimately may not be used for diagnosis and may necessitate a new recording with a correspondingly accumulated entire dose for the patient. This is advantageous for the case of a dose-intensive intraoperative 3D imaging, for example.

The system and method described in the present embodiments address the use of metal detection apparatuses in the surroundings of the interventional C-arm x-ray imaging in order to protect the patient from the risks caused by ionizing radiation (e.g., from unnecessary radiation exposure). The method may be skillfully incorporated into the interventional imaging workflow, as prior to the actual 3D recording using a C-arm, a test run for collision avoidance generally is to be performed in any event. The present embodiments are provided in hybrid ORs, for example, in which a variety of metallic tools, wires, catheters, and cables conventionally find use; thus, the probability of a metallic object inadvertently being located in the field of view of the two-dimensional projection recording (e.g., due to a lack of attention or knowledge on the part of the medical staff) increases.

For a particularly interference-free recording of x-ray images, an x-ray imaging system that includes an x-ray source for irradiating an examination object positioned in an examination region with x-ray radiation, and an x-ray detector for converting the x-ray radiation into image data of the examination object is provided. The x-ray source and the x-ray detector are arranged on an adjustable mount. The x-ray imaging system has a metal detection apparatus for detecting metal objects that are arranged at least partially within the three-dimensional field of view of the x-ray detector. A corresponding method for automatic metal inspection during the recording of x-ray images using an x-ray imaging system includes receiving an instruction to record at least one x-ray image, activating the metal detection apparatus, and scanning the field of view of the x-ray detector for metallic objects using the metal detection apparatus. The method also includes outputting a display or a signal in the event of a detection of a metallic object.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An x-ray imaging system comprising:
an x-ray source for irradiating an examination object positioned in an examination region with x-ray radiation;
an x-ray detector for converting the x-ray radiation into image data of the examination object;
an adjustable mount on which the x-ray source and the x-ray detector are arranged; and
a metal detector configured to detect metal objects that are arranged at least partially within a field of view of the x-ray detector, the detection of metal objects being prior to the x-ray source irradiating the examination object with the x-ray radiation.

2. The x-ray imaging system of claim 1, wherein the adjustable mount, on which the x-ray source and the x-ray detector are arranged, comprises a C-arm.

3. The x-ray imaging system of claim 1, wherein the metal detector is arranged indirectly or directly on the adjustable mount.

4. The x-ray imaging system of claim 3, wherein the metal detector is arranged indirectly or directly on the x-ray detector, the x-ray source, or a C-arm flange.

5. The x-ray imaging system of claim 1, wherein the metal detector comprises a metal detector probe.

6. The x-ray imaging system of claim 1, wherein the metal detector comprises a metal detector cabinet.

7. The x-ray imaging system of claim 1, further comprising a patient couch for positioning the examination object, wherein the metal detector is arrangeable on or in the patient couch.

8. The x-ray imaging system of claim 1, wherein the x-ray imaging system is an angiography system configured to:
record a variety of two-dimensional projection images; and
reconstruct the variety of two-dimensional projection images into a volume image.

9. A method for automatic metal inspection during recording of x-ray images using an x-ray imaging system, the x-ray imaging system comprising an x-ray source for irradiating an examination object positioned in an examination region with x-ray radiation, an x-ray detector for converting the x-ray radiation into image data of the examination object, an adjustable mount on which the x-ray source and the x-ray detector are arranged, and a metal detector arranged on the adjustable mount, the metal detector configured to detect metal objects that are arranged at least partially within a field of view of the x-ray detector prior to the x-ray source irradiating the examination object with the x-ray radiation, the method comprising:
receiving an instruction to record at least one x-ray image;
activating the metal detector and scanning the field of view of the x-ray detector for metallic objects by the metal detector; and
outputting a display or a signal when a metallic object is detected.

10. The method of claim 9, further comprising:
outputting a query regarding a continuation of the method;
receiving a positive instruction or a negative instruction for continuing the method; and
recording at least one x-ray image of the examination object when the positive instruction is received.

11. The method of claim 9, further comprising:
repeating the activating of the metal detector and the scanning of the field of view of the x-ray detector until a metallic object is no longer detected; and recording at least one x-ray image of the examination object when no metallic object is detected.

12. The method of 10, further comprising:

recording a variety of two-dimensional projection images; and reconstructing the variety of two-dimensional projection images into a volume image.

13. The method of claim 12, wherein activating the metal detector and scanning the examination region using the metal detector is performed during a test run for collision avoidance of the adjustable mount.

14. The method of claim 13, wherein activating the metal detector and scanning the examination region using the metal detector is performed during a test run for collision avoidance of a C-arm of the adjustable mount.

15. The method of claim 13, wherein the test run for collision avoidance runs through at least some angulation positions of the adjustable mount for recording the variety of two-dimensional projection images without the application of x-ray radiation.

16. The method of claim 15, wherein the test run for collision avoidance runs through all of the angulation positions of the adjustable mount for recording the projection images without the application of x-ray radiation.

17. The method of claim 9, further comprising determining a position of the metallic object when the metallic object is detected.

\* \* \* \* \*